United States Patent
Mori et al.

(10) Patent No.: US 10,952,695 B2
(45) Date of Patent: Mar. 23, 2021

(54) MEDICAL APPARATUS AND METHOD

(71) Applicant: Toshiba Energy Systems & Solutions Corporation, Kawasaki (JP)

(72) Inventors: Shinichiro Mori, Chiba (JP); Keiko Okaya, Setagaya (JP); Ryusuke Hirai, Shinagawa (JP); Koki Yanagawa, Tokorozawa (JP); Fumi Maruyama, Miura (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 162 days.

(21) Appl. No.: 16/223,401

(22) Filed: Dec. 18, 2018

(65) Prior Publication Data

US 2019/0183446 A1 Jun. 20, 2019

(30) Foreign Application Priority Data

Dec. 20, 2017 (JP) .............................. JP2017-244069

(51) Int. Cl.
| | |
|---|---|
| *G06K 9/00* | (2006.01) |
| *A61B 6/00* | (2006.01) |
| *G06T 7/00* | (2017.01) |
| *G06T 7/246* | (2017.01) |
| *A61N 5/10* | (2006.01) |

(52) U.S. Cl.
CPC ............ *A61B 6/5288* (2013.01); *A61B 6/463* (2013.01); *A61B 6/467* (2013.01); *A61B 6/487* (2013.01); *A61B 6/54* (2013.01); *A61N 5/1049* (2013.01); *A61N 5/1068* (2013.01); *G06T 7/0014* (2013.01); *G06T 7/246* (2017.01); *A61N 2005/1061* (2013.01); *A61N 2005/1074* (2013.01); *G06T 2207/10064* (2013.01); *G06T 2207/30004* (2013.01)

(58) Field of Classification Search
CPC ....... A61B 6/463; A61B 6/467; A61B 6/5288; A61N 2005/1061; A61N 2005/1074
USPC ........ 382/128, 131; 600/431, 436, 509, 413, 600/428, 437, 427; 623/2.11; 378/62, 65
See application file for complete search history.

(56) References Cited

U.S. PATENT DOCUMENTS

| | | | |
|---|---|---|---|
| 6,076,005 A * | 6/2000 | Sontag et al. ................ | 600/413 |
| 9,248,312 B2 | 2/2016 | Li et al. | |
| 2007/0053491 A1* | 3/2007 | Schildkraut et al. .......... | 378/65 |
| 2014/0343401 A1 | 11/2014 | Huber et al. | |
| 2016/0082284 A1 | 3/2016 | Ooga et al. | |
| 2017/0231586 A1 | 8/2017 | Hirai et al. | |

FOREIGN PATENT DOCUMENTS

| | | |
|---|---|---|
| CN | 105381525 A | 3/2016 |
| JP | 2017-144000 | 8/2017 |
| WO | WO 2005/026891 A2 | 3/2005 |
| WO | WO 2010/083415 A1 | 7/2010 |

* cited by examiner

*Primary Examiner* — Charlotte M Baker
(74) *Attorney, Agent, or Firm* — Oblon, McClelland, Maier & Neustadt, L.L.P.

(57) ABSTRACT

A medical apparatus according to an embodiment includes an acquirer and a selector. The acquirer is configured to acquire fluoroscopic images of an object captured in time series. The selector is configured to select reference images which include fluoroscopic images corresponding to a maximum exhalation position and a maximum inhalation position of the object from the plurality of fluoroscopic images acquired by the acquirer.

14 Claims, 8 Drawing Sheets

MEDICAL APPARATUS AND METHOD

CROSS-REFERENCE TO RELATED APPLICATION

This application is based upon and claims the benefit of priority from Japanese Patent Application No. 2017-244069 filed on Dec. 20, 2017; the entire content of which is incorporated herein by reference.

BACKGROUND OF THE INVENTION

Field of the Invention

Embodiment described herein relate generally to a medical apparatus and a method.

Description of Related Art

Therapeutic devices irradiate a patient (object) with a therapeutic beam such as a heavy particle beam or a radiation. During the irradiation with the therapeutic beam, a lesion of an object, that is, a spot to be irradiated with a therapeutic beam B may move due to respirations, heartbeat, intestinal movements, and the like. Examples of therapeutic methods for coping with such movement include gated irradiation method and a tracking irradiation method.

When a lesion which moves due to respirations is irradiated with a therapeutic beam, there is a need to perform irradiation synchronously with respiratory phases of an object. Techniques of respiratory phase synchronization include a technique of ascertaining the respiratory phase (external respiratory synchronization) by utilizing output values of various sensors attached to the body of an object, and a technique of ascertaining the respiratory phase (internal respiratory synchronization) based on a fluoroscopic image of an object. The processing for respiratory phase synchronization is performed by a medical apparatus which outputs a control signal to a therapeutic device. For example, a medical apparatus controls a therapeutic device by performing wired or wireless communication with the therapeutic device.

When synchronization is performed with respect to the respiratory phase of an object through internal respiratory synchronization, a plurality of fluoroscopic images of the object are captured before a therapy. Then, the position of a tumor is identified from the fluoroscopic images of the object captured during the therapy, with reference to the image pattern of a lesion position in the object imaged in the plurality of captured fluoroscopic images. In internal respiratory synchronization, a reference image selected from the plurality of captured fluoroscopic images is used. For example, a plurality of reference images are selected. As reference images used in internal respiratory synchronization, for example, fluoroscopic images corresponding to a maximum exhalation position and a maximum inhalation position of an object are used. A fluoroscopic image corresponding to a moment at which respirations of the object are in disorder due to coughing or the like may result in an external disturbance. Therefore, such fluoroscopic images are excluded from selection targets for the reference image, for example. However, work of selecting a reference image from a plurality of selection images is troublesome, and the convenience thereof is not high (refer to Japanese Unexamined Patent Application, First Publication No. 2017-144000).

SUMMARY OF THE INVENTION

An object to be achieved by the present invention is to provide a medical apparatus and a method, in which convenience at the time of selecting a reference image from a plurality of fluoroscopic images can be improved.

A medical apparatus according to an embodiment includes an acquirer and a selector. The acquirer acquires fluoroscopic images of an object captured in time series. The selector selects reference images which include fluoroscopic images corresponding to a maximum exhalation position and a maximum inhalation position of the object from the plurality of fluoroscopic images acquired by the acquirer.

According to the present embodiment, it is possible to provide a medical apparatus and a method, in which convenience at the time of selecting a reference image from a plurality of fluoroscopic images can be improved.

DETAILED DESCRIPTION OF THE INVENTION

Hereinafter, a medical apparatus and a method according to an embodiment will be described with reference to the drawings. In this application, the expression "based on XX" denotes "based on at least XX" and also includes a case based on another element in addition to XX. The expression "based on XX" is not limited to a case of directly adopting XX and also includes a case based on a result realized by performing computation or processing with respect to XX. The term "XX" indicates an arbitrary element (for example, arbitrary information).

<Configuration>

Figure 1:
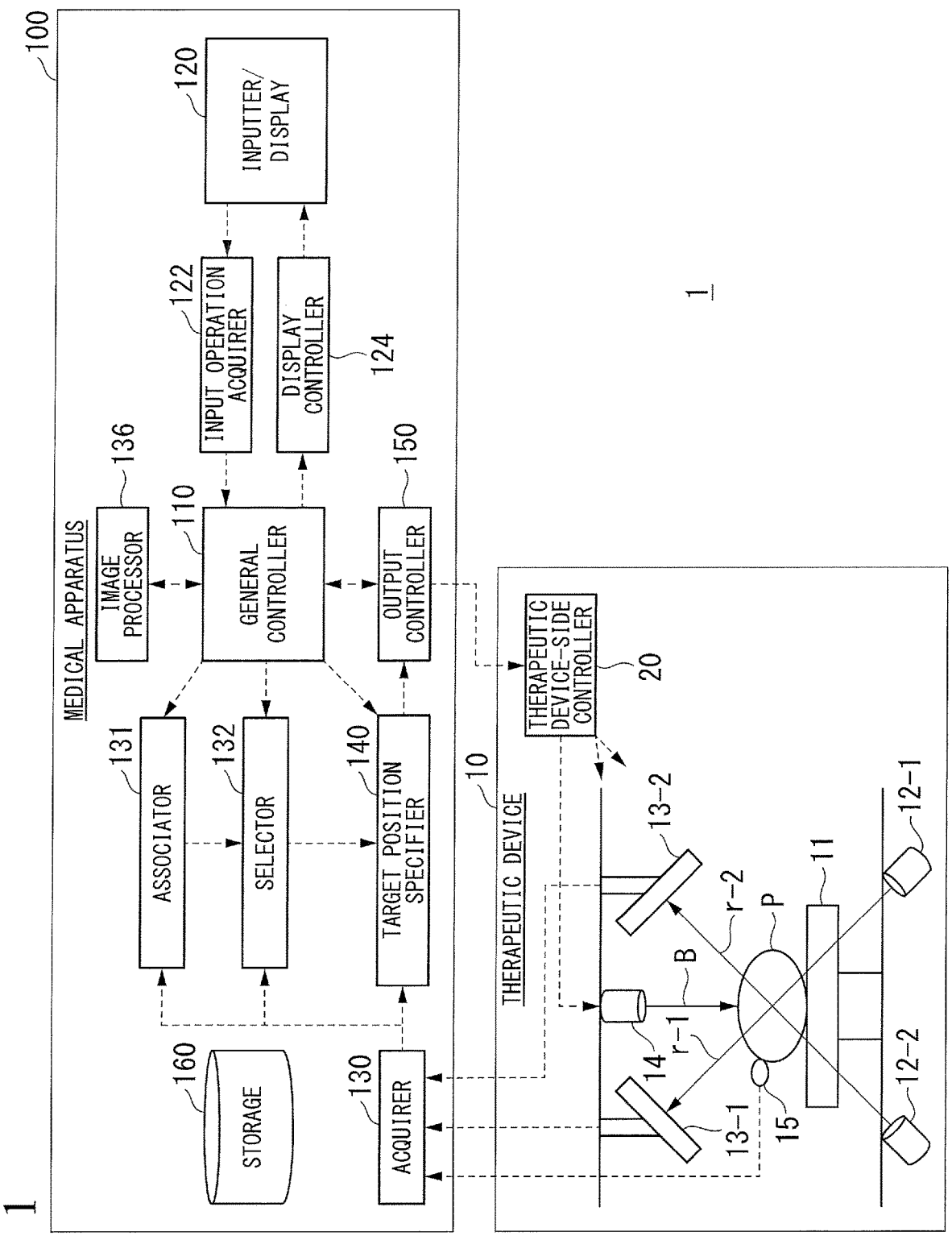
FIG. 1 is a configuration diagram of a therapy system 1 including a medical apparatus 100.

FIG. 1 is a configuration diagram of a therapy system 1 including a medical apparatus 100. For example, the therapy system 1 includes a therapeutic device 10 and the medical apparatus 100.

For example, the therapeutic device 10 includes a bed 11, radiation sources 12-1 and 12-2, detectors 13-1 and 13-2, an irradiation gate 14, a sensor 15, and a therapeutic device-side controller 20. Hereinafter, a hyphen and a numeral following it in the reference sign indicate a fluoroscopic radiation or a fluoroscopic image realized by a set of a radiation source and a detector. Suitably, the hyphen and the numeral following it in the reference sign may be omitted in description.

A object P to be treated is fixed to the bed 11. The radiation source 12-1 irradiates the object P with a radiation r—1. The radiation source 12-2 irradiates the object P with a radiation r–2 at an angle different from that of the radiation source 12-1. The radiations r–1 and r–2 are examples of electromagnetic waves and are X-rays, for example. Hereinafter, description will be given on this premise.

The radiation r–1 is detected by the detector 13-1, and the radiation r–2 is detected by the detector 13-2. For example, the detectors 13-1 and 13-2 are flat panel detectors (FPD), image intensifiers, or color image intensifiers. The detector 13-1 detects energy of the radiation r–1, performs digital conversion, and outputs the conversion result to the medical apparatus 100 as a fluoroscopic image TI-1. The detector 13-2 detects energy of the radiation r–2, performs digital conversion, and outputs the conversion result to the medical apparatus 100 as a fluoroscopic image TI-2. In FIG. 1, two sets of the radiation source and the detector are illustrated. However, the therapeutic device 10 may include three or more sets of the radiation source and the detector.

In a therapy stage, the irradiation gate 14 irradiates the object P with a therapeutic beam B. Examples of the therapeutic beam B include a heavy particle beam, an X-ray, a γ-ray, an electron beam, a proton beam, and a neutron beam. In FIG. 1, only one irradiation gate 14 is illustrated. However, the therapeutic device 10 may include a plurality of irradiation gates.

The sensor 15 is provided to recognize an external respiratory phase of the object P and is attached to the body of the object P. For example, the sensor 15 is a pressure sensor. The sensor 15 detects a pressure received from the object P, based on a voltage value (detection value). A voltage value detected by the sensor 15 corresponds to the external respiratory phase.

The therapeutic device-side controller 20 operates the radiation sources 12-1 and 12-2, the detectors 13-1 and 13-2, and the irradiation gate 14 in response to a control signal from the medical apparatus 100.

For example, the medical apparatus 100 includes a general controller 110, an input/display 120, an input operation acquirer 122, a display controller 124, an acquirer 130, an associator 131, a selector 132, an image processor 136, a target position identifier 140, an output controller 150, and a storage 160. For example, at least a part of each of the general controller 110, the input operation acquirer 122, the display controller 124, the acquirer 130, the associator 131, the selector 132, the target position identifier 140, and the output controller 150 is realized by a hardware processor such as a central processing unit (CPU) or a graphics processing unit (GPU) executing a program (software) stored in the storage 160. A part or all of these constituent elements may be realized by hardware (circuit section; including circuitry) such as a large scale integration (LSI), an application specific integrated circuit (ASIC), a field-programmable gate array (FPGA), or a graphics processor (GPU) or may be realized by cooperation of software and hardware.

Hereinafter, the function of each part of the medical apparatus 100 will be described. In description of the medical apparatus 100, unless otherwise identified, processing performed with respect to the fluoroscopic image TI will be regarded to be executed in parallel with both the fluoroscopic images TI-1 and TI-2. The general controller 110 generally controls the functions of the medical apparatus 100.

For example, the input/display 120 includes a display device such as a liquid crystal display (LCD), an organic electroluminescence (EL) display device, or a light emitting diode (LED) display; and an input device which receives an input operation performed by an operator. The input/display 120 may be a touch panel in which a display device and an input device are integrally formed or may include an input device such as a mouse and a keyboard.

The input operation acquirer 122 recognizes the details of an operation (touching, flicking, swiping, clicking, dragging, key-inputting, or the like) performed with respect to the input/display 120 and outputs the details of the recognized operation to the general controller 110. The display controller 124 causes the input/display 120 to display an image in response to an instruction from the general controller 110. The display controller 124 causes the input/display 120 to display an interface screen for receiving an instruction to start each of a preparation stage of a therapy and an irradiation stage of the therapeutic beam B. Displaying of an image includes generation of elements of an image performed based on a computation result and allocation of elements of an image made in advance to a display screen.

The acquirer 130 acquires the fluoroscopic image TI from the therapeutic device 10. The acquirer 130 acquires a detection value of the sensor 15 and acquires an external respiratory waveform based on a detection value output from the sensor 15. The acquirer 130 acquires three-dimensional volume data of the object P from a medical inspection device (not illustrated).

The associator 131 associates the fluoroscopic image TI acquired by the acquirer 130 from the therapeutic device 10 with a three-dimensional position (X, Y, and Z-coordinates) or the like of a target obtained by analyzing a change in the fluoroscopic image TI. A target may be a lesion of the object P, that is, a position to be irradiated with the therapeutic beam B, or may be a marker or a characteristic spot of the object P. Since the difference between a characteristic spot such as the diaphragm, the heart, or a bone and surrounding spots appears in a relatively clear manner in the fluoroscopic image TI, the characteristic spot is a spot of which the position can be easily identified when a computer analyzes the fluoroscopic image TI. The associator 131 may adopt a detection value (respiratory phase) acquired from the sensor 15 as a tracking value and may associate the fluoroscopic image TI acquired by the acquirer 130 from the therapeutic device 10 with a detection value (respiratory phase) acquired from the sensor 15.

The selector 132 selects a reference image to be used for identifying a target position from the fluoroscopic images TI with which the target position is associated by the associator 131. The reference images selected by the selector 132 include the fluoroscopic images TI corresponding to a maximum exhalation position and a maximum inhalation position of the object P. The fluoroscopic image TI corresponding to a respiratory phase at the time the object P coughs, sneezes, or vigorously moves is excluded. These will be further described below. The selector 132 may select the fluoroscopic image TI before being associated with the target position by the associator 131, and the selected fluoroscopic image TI may be associated with the target position by the associator 131.

The image processor 136 performs image processing such as deformable registration and a digitally reconstructed radiograph (DRR) image generation. Deformable registration is processing performed with respect to time-series three-dimensional volume data, in which positional information designated for three-dimensional volume data at a certain point of time is deployed in three-dimensional volume data at another point of time. A DRR image is a virtual fluoroscopic image generated from three-dimensional volume data to correspond to a radiation when it is assumed that irradiation of this radiation is performed from a virtual radiation source with respect to the three-dimensional volume data.

The target position identifier 140 identifies the position of a target in the fluoroscopic image TI by using a reference image selected by the selector 132 as a clue. The target position may be one point or a region having a two-dimensional or three-dimensional spread.

The output controller 150 outputs an irradiation permission signal to the therapeutic device 10 based on the target position identified by the target position identifier 140. For example, in a gated irradiation method, when the target position is settled within a gating window, the output controller 150 outputs a gate-on signal to the therapeutic device 10. A gating window is a region set in a two-dimensional plane or a three-dimensional space and is an example of an irradiation permission range. A gate-on signal is a signal for instructing an operator to irradiate the object P with the therapeutic beam B and is an example of an irradiation permission signal. Hereinafter, description will be given on these premises. The therapeutic device 10 performs irradiation of the therapeutic beam B when a gate-on signal is input, and does not perform irradiation of the therapeutic beam B when no gate-on signal is input. The irradiation permission range is not limited to a fixedly set range and may be a range which moves in a manner following a movement of a lesion.

For example, the storage 160 is realized by a random access memory (RAM), a read only memory (ROM), a hard disk drive (HDD), or a flash memory. The storage 160 stores time-series three-dimensional CT images (hereinafter, 4D CT images), the fluoroscopic image TI, an output value of the sensor 15, and the like, in addition to the program described above.

<Flow of Therapy>

Hereinafter, a flow of a therapy of the therapy system 1 will be described. A therapy of the therapy system 1 is performed in a manner of being divided into a plurality of stages, such as a planning stage, a positioning stage, the preparation stage, and the therapy stage.

Here, the flow of a therapy in each stage will be described. For example, the therapy system 1 can perform a therapy by switching between three modes, such as markerless tracking and marker tracking which are internal respiratory synchronization, and external respiratory synchronization. Here, markerless tracking will be described. Markerless tracking includes a technique of using a template matching method or machine learning. Hereinafter, markerless tracking using the template matching method will be described, and description will be given such that the gated irradiation method is employed as an irradiation method. The medical apparatus 100 may be switchable between the template matching method and a technique using machine learning.

[Planning Stage]

In the planning stage, first, CT imaging of the object P is performed. In CT imaging, images of the object P are captured in various directions for each of various respiratory phases. Next, 4D CT images are generated based on the results of the CT imaging. 4D CT images are n three-dimensional CT images (an example of the three-dimensional volume data described above) arranged in time series. A period obtained by multiplying this number n by the time interval between the time-series images is set to cover a period in which the respiratory phase changes by one cycle, for example. 4D CT images are stored in the storage 160.

Next, a physician, a radiologist, or the like inputs a contour with respect to one CT image of n CT images, for example. This contour is a contour of a tumor which is a lesion or a contour of an organ which is not intended to be irradiated with the therapeutic beam B. Next, for example, the image processor 136 sets the contour for each of n CT images through deformable registration. Next, a therapeutic plan is decided. A therapeutic plan is a plan for regulating irradiation of the place, the direction, and the quantity of the therapeutic beam B in accordance with the position of a lesion based on information of the set contour. The therapeutic plan is decided in accordance with a therapeutic method such as the gated irradiation method or a tracking irradiation method. A part or all of the processing in the planning stage may be executed by an external device. For example, processing of generating 4D CT images may be executed by a CT device.

Here, a region defined by the contour of a tumor, the center of gravity in this region, the position of a characteristic spot of the object P, or the like becomes a target position. Moreover, in the therapeutic plan, the position which may be irradiated with the therapeutic beam B is decided as a target position. When the contour is set through deformable registration, a margin is automatically or manually set for the target position, and a gating window is set by applying the margin. This margin is provided to absorb an error in the device, positioning, and the like.

[Positioning Stage]

In the positioning stage, the bed position is adjusted. The object P is laid on the bed 11 and is fixed by using a shell or the like. First, the bed position is roughly adjusted. In this stage, a worker visually checks for the position and the posture of the object P and moves the bed 11 to a position at which the object P will be irradiated with the therapeutic beam B from the irradiation gate 14. Accordingly, the position of the bed 11 is roughly adjusted. Next, an image to be utilized for minutely adjusting the bed position is captured. For example, when 3D-2D registration is performed, the fluoroscopic image TI is captured. For example, the fluoroscopic image TI is captured at the timing of the end of exhalation of the object P. Since the position of the bed 11 has already been roughly adjusted, an area near a lesion of the object P is imaged in the fluoroscopic image TI.

When 3D-2D registration is performed, in this stage, a DRR image is generated from three-dimensional volume data by using the radiation sources 12-1 and 12-2, the detectors 13-1 and 13-2, and the therapeutic plan information of the object P. The movement amount of the bed is calculated based on the DRR image and the fluoroscopic image TI, and the bed 11 is moved. The position of the bed 11 is minutely adjusted by repeating capturing the fluoroscopic image TI, calculating the movement amount of the bed, and moving the bed 11.

[Preparation Stage (Part 1)]

When the positioning stage ends, the processing shifts to the preparation stage. First, a DRR image of each phase is made from 4D CT images. The DRR image may be made at any time after the 4D CT images have been captured. In this case, a position, at which the gating window set in the therapeutic plan is projected, is set as the gating window on the DRR image. In the preparation stage, first, the fluoroscopic image TI which becomes a target to be selected as a reference image is captured. When the fluoroscopic image TI is captured, a physician or the like instructs the object P to perform deep respirations a plurality of times (twice or more), for example. While the object P performs deep respirations a plurality of times in accordance with the instruction of a physician or the like, the fluoroscopic image TI is captured such that two respirations of the object P are covered. While the object P performs deep respirations, an external respiratory waveform of the object P is acquired synchronously with the fluoroscopic image TI. The display controller 124 causes the input/display 120 to display the acquired external respiratory waveform. A tracking value based on the respiratory phase of the object P obtained from the external respiratory waveform is associated with the captured fluoroscopic image TI.

In this stage, the relationship between the fluoroscopic image TI and the target position is learned from information of the DRR image and the target position on the DRR image. Moreover, correction of the target position by a physician is received. From the fluoroscopic image TI in which the target position has been learned, one or more reference images are selected based on the tracking value, and a template is generated from the selected reference image. A template may be the fluoroscopic image TI itself which becomes a reference image or may be a cut-out characteristic part of this fluoroscopic image TI. Learning of the target position may be performed at any timing during a period from the planning stage to the therapy stage. For example, when a template is made from the fluoroscopic image TI for one respiration of the first half of the fluoroscopic images TI for two respirations of the object P, whether a target can be tracked with the fluoroscopic image TI for one respiration of the second half may be checked by using the template. In this case, the display controller 124 may cause the gating window set on the DRR image to be displayed on the fluoroscopic image TI.

[Preparation Stage (Part 2)]

Capturing the fluoroscopic image TI is restarted. The target position identifier 140 performs matching of the template with respect to the fluoroscopic images TI input in time series and allocates the target position with respect to the fluoroscopic image TI. While causing the input/display 120 to display the fluoroscopic images TI as a moving image, the display controller 124 causes the target position to be displayed in a manner of being superimposed on a frame of the fluoroscopic image TI in which the target position is allocated. As a result, the tracking results of the target position are checked by a physician or the like.

In this case, the display controller 124 causes the gating window set on the DRR image to be displayed on the fluoroscopic image TI. The output controller 150 determines whether or not the target position is settled within the gating window, regarding both the fluoroscopic images TI-1 and TI-2. In the therapy stage, a gate-on signal is output to the therapeutic device 10 when the target position is settled within the gating window. However, in the preparation stage, the presence or absence of an output of a gate-on signal is transmitted to the display controller 124 via the general controller 110. The display controller 124 causes the input/display 120 to display the presence or absence of an output of a gate-on signal in parallel with displaying of the moving image. As a result, the output timing of a gate-on signal is checked by a physician or the like.

[Therapy Stage]

In the therapy stage, the display controller 124 causes the gating window set on the DRR image to be displayed on the fluoroscopic image TI. The output controller 150 outputs a gate-on signal to the therapeutic device 10 when the target position is settled within the gating window, regarding both the fluoroscopic images TI-1 and TI-2. Accordingly, a therapy is performed by irradiating a lesion of the object P with the therapeutic beam B. In the case in which the target position is the position of a lesion, irradiation of the therapeutic beam B is performed when the tracked target position is settled within the gating window. In the case in which the target position is the position of a characteristic spot of the object P, irradiation of the therapeutic beam B is performed when the position of a lesion derived out from the target position is settled within the gating window, based on the relationship between the target position learned in advance and the position of a lesion. A portion at the position of a lesion may be irradiated with the therapeutic beam B by these complex techniques. That is, irradiation of the therapeutic beam B may be performed when a lesion is settled within a first gating window and a characteristic spot is settled within a second gating window, by setting each of the position of a lesion and the position of a characteristic spot as the target position.

<Display Image and Flowchart>

Hereinafter, processing of the medical apparatus 100 for supporting the flow of a therapy described above will be described.

Figure 2:
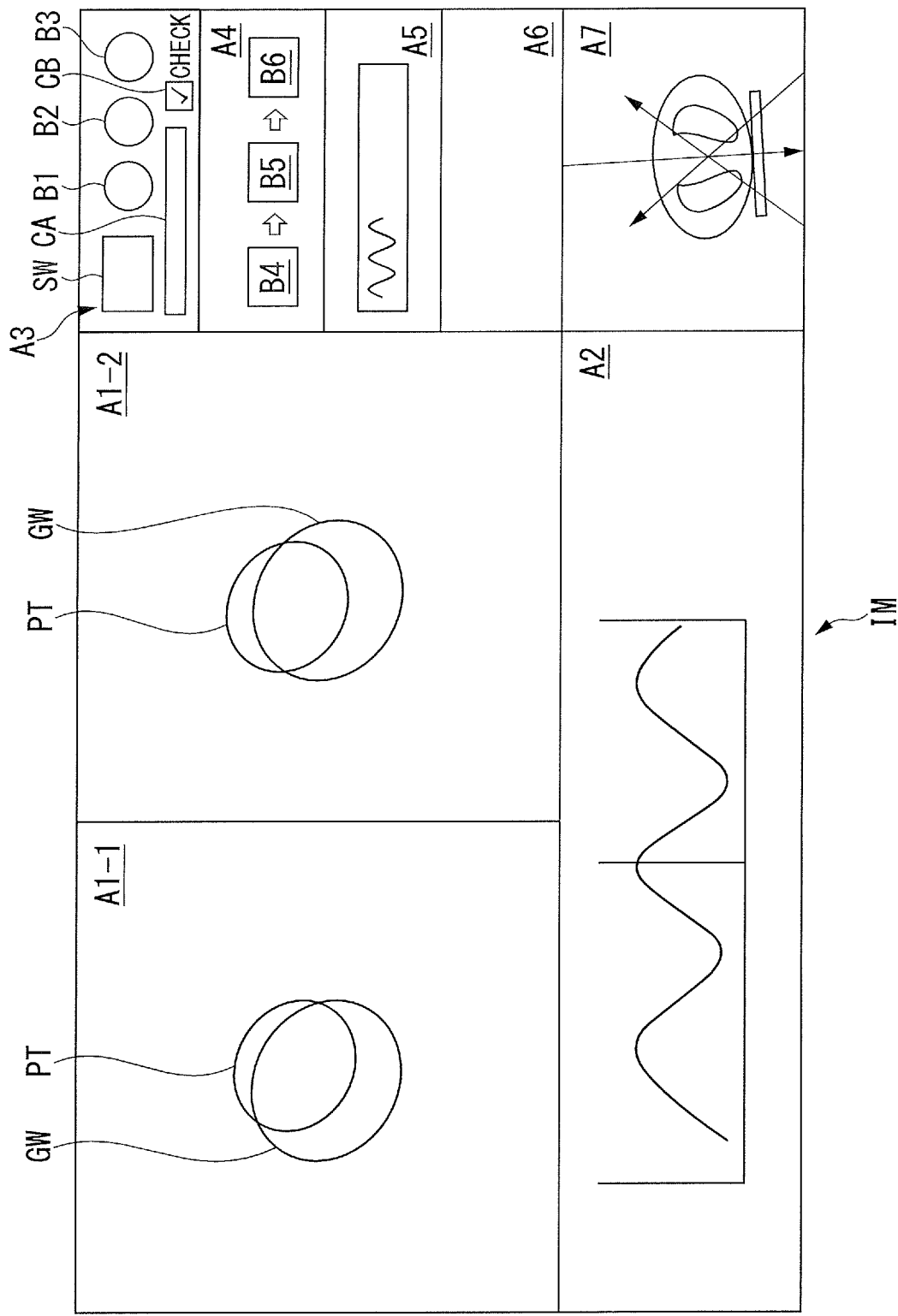
FIG. 2 is a view illustrating an example of an interface image IM displayed by an input/display 120 of the medical apparatus 100.

FIG. 2 is a view illustrating an example of an interface image IM which is displayed by the input/display 120 of the medical apparatus 100. For example, the interface image IM includes regions A1-1, A1-2, A2, A3, A4, A5, A6, and A7.

In the region A1-1, a gating window GW or a target position PT is displayed in a manner of being superimposed on the fluoroscopic image TI-1. In the region A1-2, the gating window GW or the target position PT is displayed in a manner of being superimposed on the fluoroscopic image TI-2. In the region A2, various graphs of the external respiratory waveform, the target position, an output of a gate signal, and the like are displayed.

In the region A3, a selection window SW for receiving selection of a mode and the like, a first button B1 for instructing the therapeutic device 10 to start capturing or stop capturing the fluoroscopic image TI, a second button B2 for instructing the therapeutic device 10 to temporarily stop capturing the fluoroscopic image TI, a third button B3 for instructing the therapeutic device 10 to end a therapeutic session, a slide bar for tracing back and checking for DRR images or the fluoroscopic images TI in time series, a control area CA in which a frame advancing switch and the like are set, a check box CB for checking for completion of the preparation stage, and the like are set. For example, an operation with respect to each part of the interface image IM is performed by performing a touching operation, clicking a mouse, operating a keyboard, or the like. For example, the first button B1 is operated by performing a touching operation or clicking a mouse.

In the region A4, a fourth button B4, a fifth button B5, and a sixth button B6 for instructing the therapeutic device 10 that the therapy stage corresponding to the mode proceeds to a next step are set. In the region A5, the graph of the external respiratory waveform based on the output value of the sensor 15, and the like are displayed. In the region A6, an image indicating the therapeutic plan information of the object P, and text information are displayed. In the region A7, the irradiation direction of an X-ray, the irradiation field, the irradiation direction of the therapeutic beam B, the contour of a target, the marker ROI, and the like are displayed in a manner of being superimposed on a cross section of a CT image of the object P.

Figure 3:
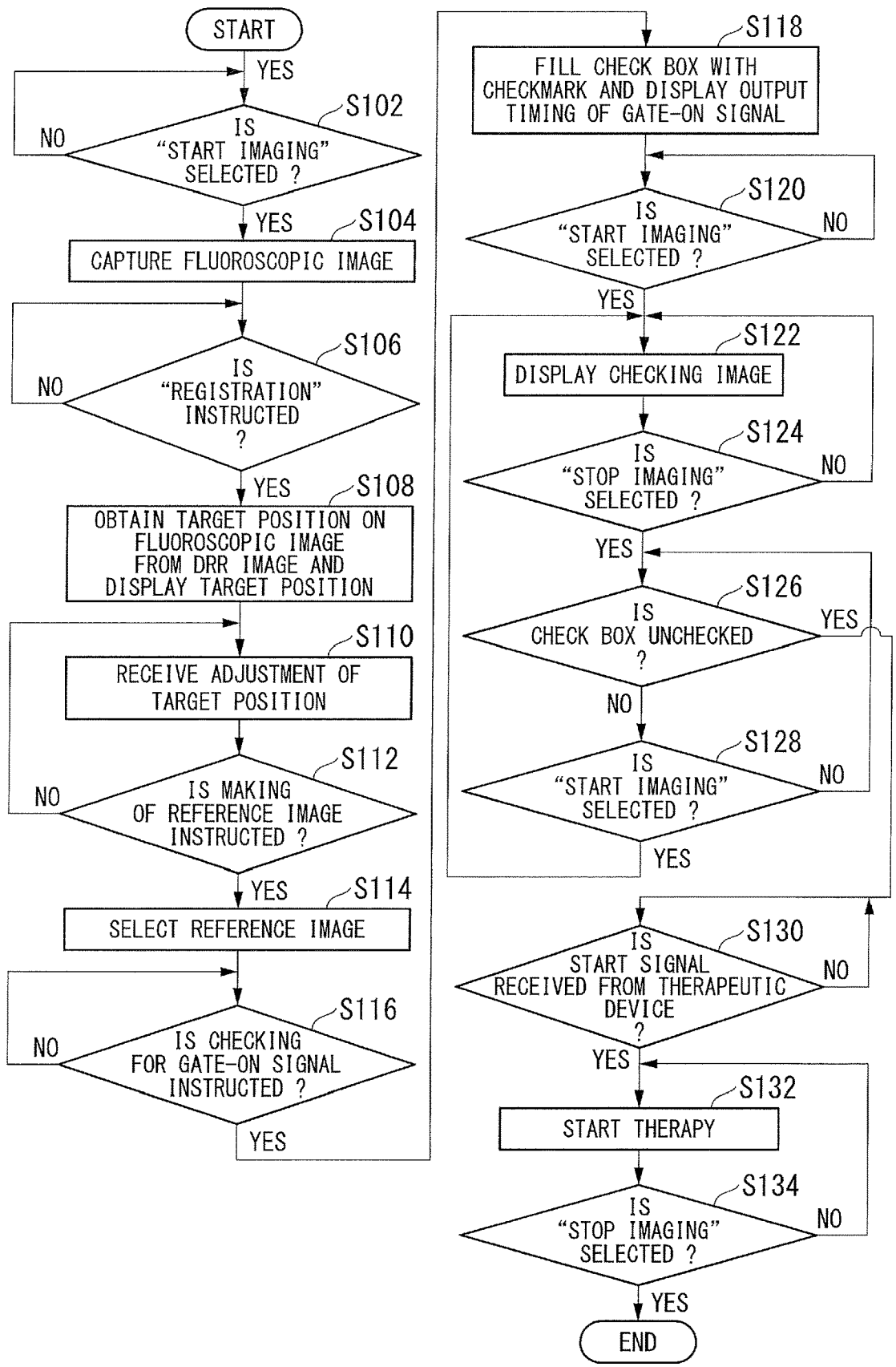
FIG. 3 is a view illustrating an example of a flowchart of a flow of processing executed by the medical apparatus 100.

Hereinafter, various functions of the interface image IM will be described with reference to the flowchart. FIG. 3 is a flowchart (Part 1) illustrating an example of a flow of processing executed by the medical apparatus 100. In the following description, when it is detected that an operation has been performed with respect to the medical apparatus 100, the general controller 110 is regarded to perform determination with reference to information input from the input operation acquirer 122, and description for each case will be omitted.

Figure 4:
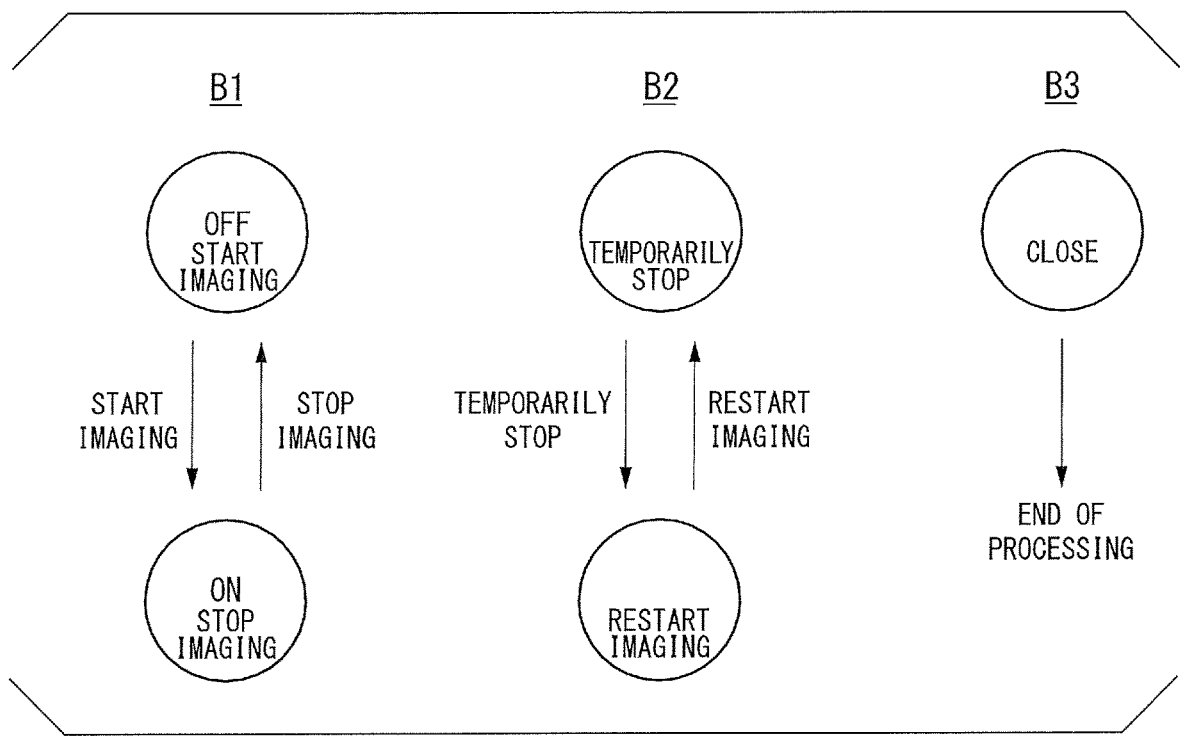
FIG. 4 is a view illustrating a change in a form of displaying a first button B1, a second button B2, and a third button B3.

First, with reference to the information input from the input operation acquirer 122, the general controller 110 determines whether or not start imaging is selected by operating the first button B1 (Step S102). FIG. 4 is a view illustrating a change in a form of displaying the first button B1, the second button B2, and the third button B3. As illustrated in the diagram, in an initial state, the first button B1 indicates a state in which imaging is "OFF", that is, stopped in a form of receiving an instruction of "start imaging". When the first button B1 is operated, a state in which imaging is "ON", that is, executed is indicated, and the first button B1 changes into a form of receiving an instruction of "stop imaging". The first button B1 performs state transition between these two forms.

In an initial state, the second button B2 is in a form of receiving an instruction of "temporary stop" of imaging when being operated. When being operated, the second button B2 changes into a form of receiving an instruction of "restart imaging". In an initial state, the third button B3 is in a form of receiving an instruction of "closing" of the interface image IM. When the third button B3 is operated, the interface image IM is stopped being displayed, and a series of processing ends.

When start imaging is selected by operating the first button B1, the general controller 110 instructs the output controller 150 to instruct the therapeutic device 10 to capture the fluoroscopic image TI which becomes a template (Step S104). For example, the output controller 150 instructs the therapeutic device 10 to capture the fluoroscopic images TI for k times of respirations.

Figure 5:
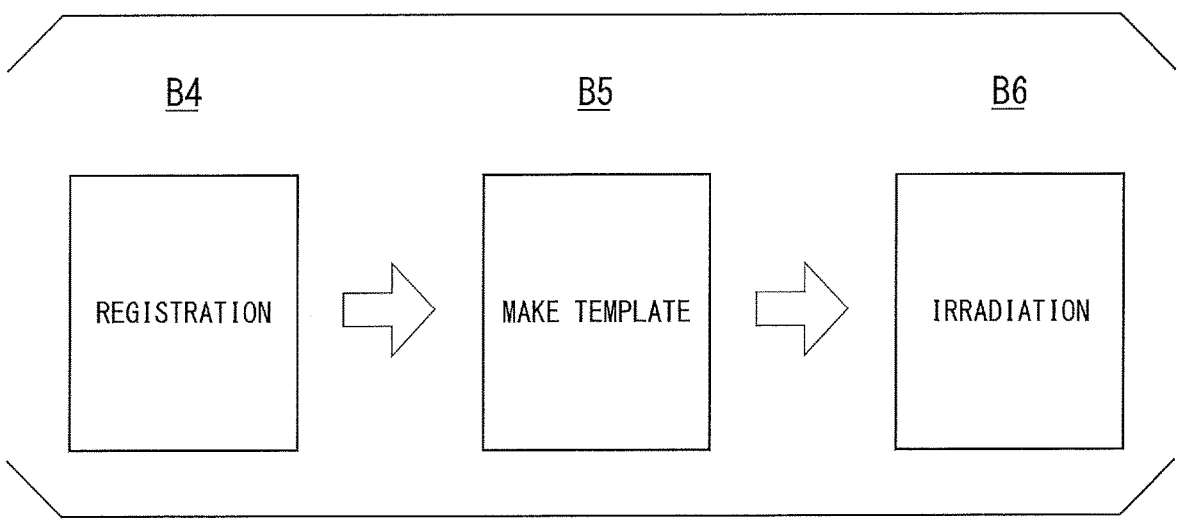
FIG. 5 is a view illustrating details of a fourth button B4, a fifth button B5, and a sixth button B6.

Next, the general controller 110 determines whether or not registration is instructed by operating the fourth button B4 (Step S106). FIG. 5 is a view illustrating details of the fourth button B4, the fifth button B5, and the sixth button B6. The fourth button B4 receives an instruction of registration (learning of the target position PT in the fluoroscopic image TI), the fifth button B5 receives an instruction of selecting a reference image, and the sixth button B6 receives an instruction of checking for a gate-on signal.

When registration is instructed by operating the fourth button B4, the general controller 110 instructs the associator 131 to obtain a target position in the fluoroscopic image TI from the target position PT in a DRR image, and instructs the display controller 124 to cause the input/display 120 to display the obtained target position PT in a manner of being superimposed on the fluoroscopic image TI (Step S108). As described above, the image processor 136 performs processing of matching characteristic portions in images between the DRR image of which the target position PT is already known and the fluoroscopic image TI, based on the DRR image made from a CT image captured in the planning stage, or the fluoroscopic image TI captured after the planning stage, thereby deriving out the target position PT in the fluoroscopic image TI. The relationship between the fluoroscopic image TI and the target position PT is provided for the associator 131. An image in which the target position PT is superimposed on the fluoroscopic image TI is displayed in the regions A1-1 and A1-2 of the interface image IM, for example. In this state, the general controller 110 receives an adjustment of the target position (Step S110). For example, the target position PT is adjusted by performing a drag/drop operation with respect to the regions A1-1 and A1-2. When the target position PT is adjusted, the general controller 110 provides the adjusted relationship between the fluoroscopic image TI and the target position PT for the associator 131.

Next, the general controller 110 determines whether or not selecting a reference image is instructed by operating the fifth button B5 (Step S112). When the fifth button B5 is operated, the general controller 110 instructs the selector 132 to select a reference image (Step S114). The selector 132 selects a reference image from the fluoroscopic images TI and stores the selected reference image in the storage 160.

Next, the general controller 110 determines whether or not checking for a gate-on signal is instructed by operating the sixth button B6 (Step S116). When checking for a gate-on signal is instructed, the general controller 110 instructs the display controller 124 to change the check box CB into a state filled with checkmark (Step S118). In the state in which the check box CB is filled with checkmark, the output timing of a gate-on signal is calculated and displayed, but a gate-on signal is not actually output to the therapeutic device 10.

Next, the general controller 110 determines whether or not start imaging is selected by operating the first button B1 (Step S120). When start imaging is selected by operating the first button B1, the general controller 110 instructs the output controller 150 to instruct the therapeutic device 10 to capture the fluoroscopic image TI and instructs the display controller 124 to cause the input/display 120 to display a checking image using the captured fluoroscopic image TI (Step S122).

The checking image is displayed in the regions A1-1 and A1-2. The checking image is an image in which the target position PT or the gating window GW is superimposed on the fluoroscopic image TI which is reproduced as a moving image (refer to FIG. 2). The output controller 150 outputs a gate-on signal to the display controller 124, which displays the gate-on signal in the region A2 when the target position PT is settled in the gating window GW. A physician or the like can check for whether or not the target position PT such as a lesion of the object P is recognized as a correct position, whether or not the timing the target position PT is settled in the gating window GW is appropriate, the output efficiency of a gate-on signal, and the like, by visually recognizing this checking image. The checking image is displayed until stop imaging is selected by operating the first button B1 (Step S124). Even after stop imaging is selected, the checking image can be traced back and checked for by operating the control area CA in which the slide bar, the frame advancing switch, and the like are set.

When stop imaging is selected by operating the first button B1, the general controller 110 determines whether or not checkmark of the check box CB is canceled (Step S126). When checkmark of the check box CB is not canceled, the general controller 110 determines whether or not start imaging is selected by operating the first button B1 (Step S128). When start imaging is selected, the processing returns to Step S122, and when start imaging is not selected, the processing returns to Step S126. When checkmark of the check box CB is canceled, the general controller 110 determines whether or not a start signal is received from the therapeutic device 10 (Step S130). This start signal is a signal output when the therapeutic device 10 can start a therapy by operating a switch (not illustrated) of the therapeutic device 10. When a start signal is received from the therapeutic device 10, the general controller 110 instructs the display controller 124, the target position identifier 140, and the output controller 150 to start a therapy, and the output controller 150 instructs the therapeutic device to capture the fluoroscopic image TI (Step S132). When the check box is unchecked in Step S126, even if no start signal is received from the therapeutic device 10, the general controller 110 may determine whether start imaging is instructed by operating the first button B1. When the target position PT identified by the target position identifier 140 is settled in the gating window, a gate-on signal may be output to the therapeutic device 10 (not illustrated). In this case, the beam B is not output from the therapeutic device. When the check box has not been unchecked in Step S126 but the check box is unchecked after start imaging is selected, a gate-on signal may be output in the middle of imaging (not illustrated). The target position identifier 140 performs matching of the fluoroscopic image TI and the template, thereby identifying the target position PT. The output controller 150 causes a gate-on signal to be output to the therapeutic device 10 when the target position is settled in the gating window. The display controller 124 causes the input/display 120 to display a therapeutic image in which the target position or the gating window GW is superimposed on the fluoroscopic image TI. The therapeutic image is displayed in the regions A1-1 and A1-2. A therapy continues until stop imaging is selected by operating the first button B1 (Step S134). The medical apparatus 100 may end a therapy even when a signal of completing irradiation is received from the therapeutic device 10 or when a signal indicating that an operation of ending irradiation is conducted in the therapeutic device 10 is received from the therapeutic device 10.

The display controller 124 may change the color of the gating window when a gate-on signal is output (in the checking stage, when the conditions for outputting a gate-on signal are fulfilled) in the checking image and the therapeutic image. For example, regarding both the fluoroscopic images TI-1 and TI-2, the border line of the gating window GW may be displayed in a first color when the target position PT is not settled in the gating window GW, may be displayed in a second color when the target position PT is settled in the gating window GW in only one of both the fluoroscopic images TI-1 and TI-2, and may be displayed in a third color when the target position PT is settled in the gating window GW (that is, when the conditions for outputting a gate-on signal are fulfilled) in both the fluoroscopic images TI-1 and TI-2. An error icon may be displayed when the target position PT is not settled in the gating window GW in both the fluoroscopic images TI-1 and TI-2.

When the conditions for outputting a gate-on signal are fulfilled, the display controller 124 may change the hue or the brightness of any of an inner region or an outer region of the gating window GW. Moreover, the medical apparatus 100 may include a notifier that issues notification by a sound or a vibration when the conditions for outputting a gate-on signal are fulfilled.

The mode switching between markerless tracking, marker tracking, and external respiratory synchronization may be received at a suitable timing. For example, the mode switching may be received at an arbitrary timing over a period from the preparation stage to the therapy stage, instead of being received in the processing prior to Step S102 in the flowchart. Suitably, redoing of the processing is received. For example, in a scene displaying the checking image, an operation for redoing the processing from the step of imaging a reference image is received. When the mode switching is performed after the fluoroscopic image TI is captured, the fluoroscopic image TI which has already been captured may be employed as a template.

Figure 6:
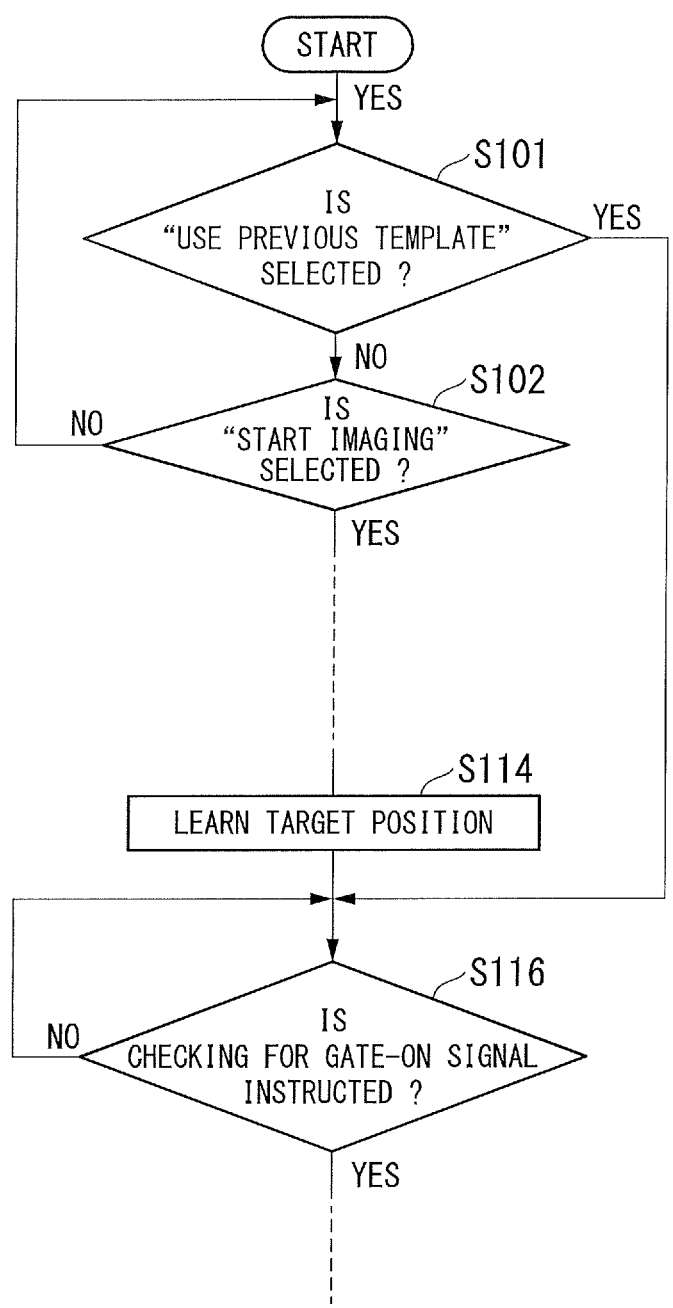
FIG. 6 is a view illustrating another example of a flowchart of a flow of processing executed by the medical apparatus 100.

When a therapy is performed in a divided manner over a plurality of times, the therapy may be performed by succeeding a template made before a previous therapy. FIG. 6 is a flowchart (Part 2) illustrating another example of a flow of processing executed by the medical apparatus 100. As illustrated, after markerless tracking is selected in the selection window SW, the general controller 110 determines whether or not "use previous template" is selected in any of the regions (Step S101). When "use previous template" is selected, the processing skips Steps S102 to S114, and the processing proceeds to Step S116.

Next, selection of a reference image performed in the preparation stage will be described. In the preparation stage, a reference image is selected from the time-series fluoroscopic images TI captured when the object P performs deep respirations. When a reference image is selected, the associator 131 associates the target position or the respiratory phase of the object P in the external respiratory waveform with the fluoroscopic image TI. Hereinafter, a selection form of a reference image will be described.

(First Selection Form of Reference Image)

First, a first selection form of a reference image will be described. All of the captured fluoroscopic images TI may be adopted as reference images. However, in a plurality of fluoroscopic images TI, when the fluoroscopic images TI similar to each other become reference images, the information may sometimes be biased. It is desired to select the fluoroscopic image TI in which such a bias of information is reduced and information of movement of a target can be efficiently obtained.

The position of a target is effectively identified by including the fluoroscopic images TI of the maximum exhalation position and the maximum inhalation position in the reference image. In the stage of selecting a reference image, the associator 131 associates the fluoroscopic image TI and the target position with each other. The fluoroscopic image TI is displayed in the region A1 of the interface image IM illustrated in FIG. 2, and a waveform α of the coordinate position (refer to FIG. 7) which is a waveform of the coordinates of the target position is displayed in the region A2. A physician or the like designates one arbitrary point in the waveform α of the coordinate position. One point Tp of the waveform α of the coordinate position is designated by touching the surface on which the waveform α of the coordinate position is displayed. The selector 132 performs setting by cutting out a designated respiration, for example, one respiration of the waveform α of the coordinate position from the one point designated by the physician or the like. In the region A2 of the interface image IM, the external respiratory waveform acquired by the sensor 15 may be displayed together with the waveform α of the coordinate position, or in place of the waveform α of the coordinate position. Instead of designating one point of the waveform α of the coordinate position, one point of the external respiratory waveform may be designated.

Figure 7:
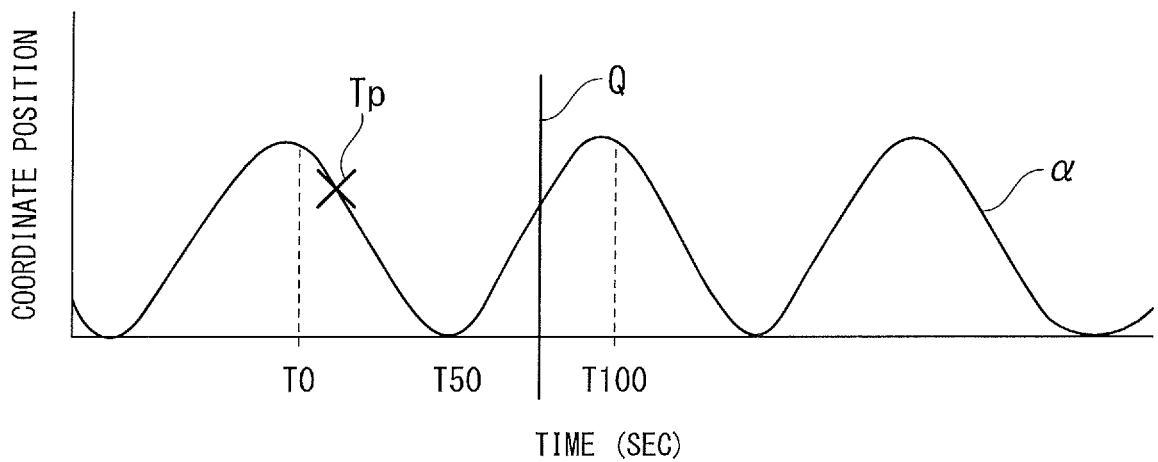
FIG. 7 is a view illustrating an example of an image displayed in a region A2 of the interface image IM in a preparation stage.

For example, it is assumed that a physician or the like has designated the one point Tp of the waveform α of the coordinate position illustrated in FIG. 7. In this case, when the respiratory phase for one respiration is cut out, the selector 132 identifies one respiration including the one point Tp designated by the physician or the like. For example, the maximum inhalation positions in the front and the rear of the maximum inhalation position close to the one point Tp is identified. The maximum exhalation indicates a state of the end of exhalation of the object P during one respiration, and the maximum inhalation indicates a state immediately before exhalation of an object during one respiration. For example, a point at which a change in the respiratory phase switches over from a negative state to a positive state, and a point at which a change in the respiratory phase switches over from a positive state to a negative state are identified as the maximum exhalation or the maximum inhalation. The maximum exhalation position and the maximum inhalation position include the switch-over points and points in the vicinity thereof within a range not impeding the implementation of the present invention. A detected position may be manually corrected by a physician or the like.

In this case, the fluoroscopic image TI corresponding to the respiratory phase, in which a cursor Q indicated in the region A2 is positioned, is displayed in the regions A1-1 and A1-2 of the interface image IM. In the example illustrated in FIG. 7, the cursor Q is displayed on a time T80 of the maximum exhalation position in the region A2 of the interface image IM. The fluoroscopic images TI-1 and TI-2 at the time T80 of the maximum exhalation position are displayed in the regions A1-1 and A1-2 of the interface image IM.

The respiratory phase identified in this manner is cut out as one respiration. The respiratory phase for one respiration may be a respiratory phase other than the respiratory phase between two maximum inhalation positions having a maximum exhalation position interposed therebetween. For example, a respiratory phase decided by having one arbitrary point Tp as a starting point or a center may be adopted, or a respiratory phase between two maximum exhalation positions having a maximum inhalation position interposed therebetween may be adopted.

For example, as illustrated in FIG. 7, the waveform α of the coordinate position is displayed in the region A2 of the interface image IM. For example, the associator 131 sets one respiration of the waveform α of the coordinate position by identifying the one point Tp designated by a physician or the like or the maximum exhalation position and the maximum inhalation position of the waveform α of the coordinate position. In the graph illustrated in FIG. 7, the vertical axis indicates the coordinate position of the target position, and the horizontal axis indicates the time. Here, the coordinate position indicated in the vertical axis is a coordinate position of any of X, Y, and Z of the target position. For example, while having a direction along the body axis of the object P as a Z-axis direction, a lateral direction as an X-axis direction, and a front-rear direction as a Y-axis direction, the coordinate position in the Z-axis direction is indicated in the vertical axis illustrated in FIG. 7. Since the Z-direction has the largest displacement among the X-direction, the Y-direction, and the Z-direction, the waveform α of the coordinate position is generated in accordance with a change in the coordinate position in the Z-direction. However, the waveform of the coordinate position may be generated in accordance with a change in the coordinate position in the X-direction or the Y-direction.

Figure 8:
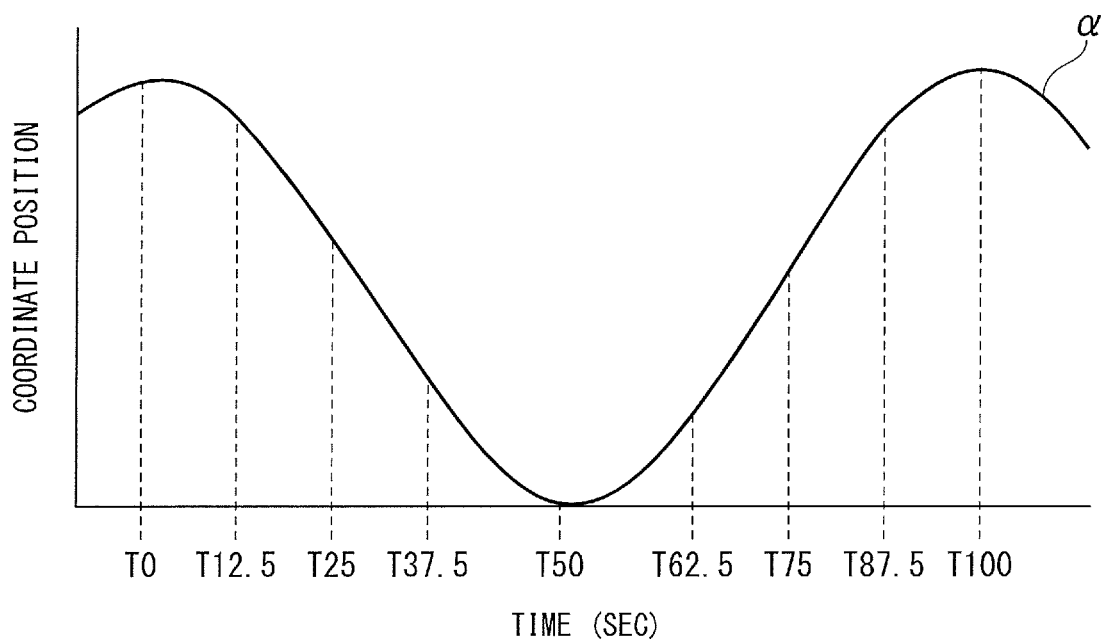
FIG. 8 is a view for describing setting one respiration of a waveform of a coordinate position.

For example, as illustrated in FIG. 8, the selector 132 selects the fluoroscopic image TI of the maximum exhalation position in the cut-out waveform α of the coordinate position for one respiration and the same number of the fluoroscopic images TI temporally in the front and the rear of the maximum exhalation position. Here, specifically, nine fluoroscopic images TI in total including four fluoroscopic images TI at times "T0", "T12.5", "T25", and "T37.5" before a time T50 of the maximum exhalation position, the fluoroscopic image TI at the time "T50" of the maximum exhalation position, and four fluoroscopic images TI at times "T62.5", "T75", "T87.5", and "T100" after the time "T50" of the maximum exhalation position are selected.

The selector 132 selects the fluoroscopic images TI, as reference images, including the fluoroscopic images TI corresponding to the maximum exhalation position and the maximum inhalation position from a plurality of fluoroscopic images TI with which the target position of the object P is associated. For example, the fluoroscopic image TI of which the respiratory phase is closest to the maximum exhalation position may be selected as the reference image, or several fluoroscopic images TI, for example, approximately three fluoroscopic images TI in the front and the rear may be selected as the reference images from an arbitrary respiratory phase such as the maximum exhalation position. A selecting method for a reference image is arbitrary. For example, in the foregoing example, all of the fluoroscopic images TI associated with the target position are selected as the reference images. However, a part of the fluoroscopic images TI associated with the respiratory phase may be selected as the reference images. The fluoroscopic images TI of the maximum exhalation position and the maximum inhalation position are images which can be more favorably used as reference images than the fluoroscopic image TI at a different position in the waveform α of the coordinate position.

A waveform for one respiration may be automatically set even if one point of the waveform α of the coordinate position is not designated by a physician or the like. For example, the maximum exhalation position and the maximum inhalation position may be identified from the waveform α of the coordinate position acquired by the sensor 15, and a portion between maximum exhalation positions in the front and the rear of an arbitrary maximum exhalation position in the waveform α of the coordinate position may be adopted as one respiration of the waveform α of the coordinate position. A respiration designated about the position of the respiratory phase may be set. The point designated by a physician or the like may be two or more points instead of one point. For example, a starting point and an ending point of the respiratory phase may be able to be designated.

When a physician or the like sets the one point Tp, in place of a form of touching a surface displaying the waveform α of the coordinate position or the position of a tumor, a setting button may be provided such that a point designated by the cursor Q can be set. A physician or the like may be able to select the fluoroscopic image TI which will become a selection candidate, by causing the cursor Q to be movable within the range of the waveform α of the coordinate position.

(Second Selection Form of Reference Image)

Figure 9:
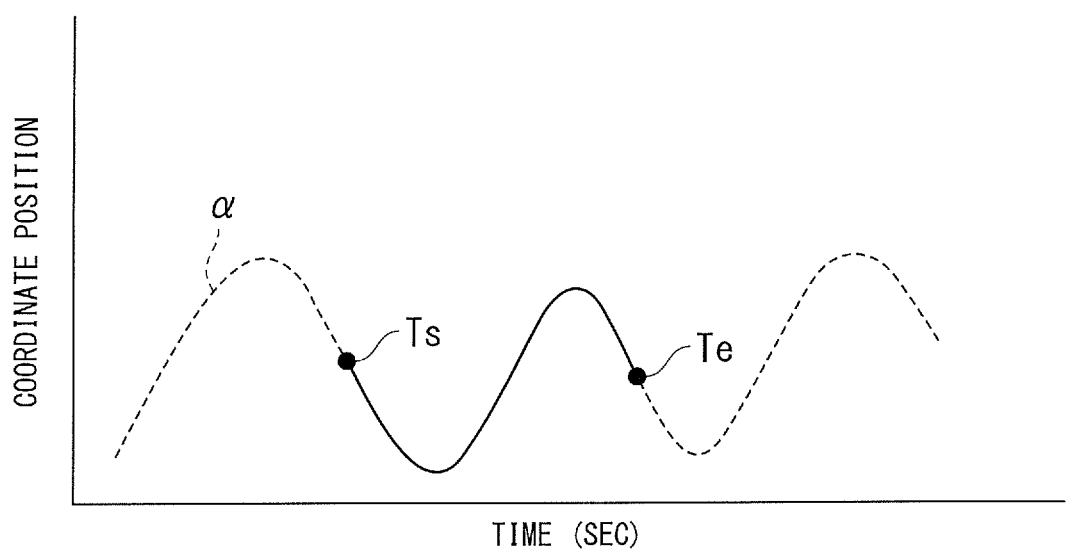
FIG. 9 is a view illustrating a modification example of a waveform of the coordinate position for selecting a reference image.

Next, a second selection form of a reference image will be described. One respiration of the waveform α of the coordinate position for selecting a reference image may be set as a respiration other than a respiration between two maximum inhalation positions having the maximum exhalation position interposed therebetween. In the second selection form, in the waveform α of the coordinate position displayed in the region A2 of the interface image IM, one point designated by a physician or the like through touching is set as the starting point, and a region to the ending point which is at the same coordinate position as the starting point from the maximum exhalation position via the maximum inhalation position (or from the maximum inhalation position via the maximum exhalation position) is set as one respiration. For example, as indicated with a dotted line in FIG. 9, one point in the waveform α of the coordinate position is set as a starting point Ts, and a region to an ending point Te which is the same coordinate position as the starting point Ts from the maximum exhalation position via the maximum inhalation position is set as one respiration. The fluoroscopic image TI which is set in this manner and is included in one respiration becomes a reference image.

Even if one respiration is set in any range in the waveform α of the coordinate position, one respiration always includes the maximum exhalation position and the maximum inhalation position. Therefore, since the fluoroscopic images TI in one respiration include the fluoroscopic images TI of the maximum exhalation position and the maximum inhalation position, these can be selected as reference images. In this form, instead of setting a respiration other than the respiration between two maximum inhalation positions having the maximum exhalation position interposed therebetween, one point of the waveform α of the coordinate position may be input, and the equal number of fluoroscopic images TI included in the range of one respiration in the front and the rear of this one point may be adopted as reference images.

(Third Selection Form of Reference Image)

Next, a third selection form of a reference image will be described. In the third form, in a case in which a designated respiration range covers a plurality of times of respirations, for example, when the maximum exhalation position and the maximum inhalation position are different from each other, a reference image is selected from a range which includes the maximum exhalation position and the maximum inhalation position and in which the difference between the coordinate positions of the maximum exhalation position and the maximum inhalation position is maximized.

Figure 10:
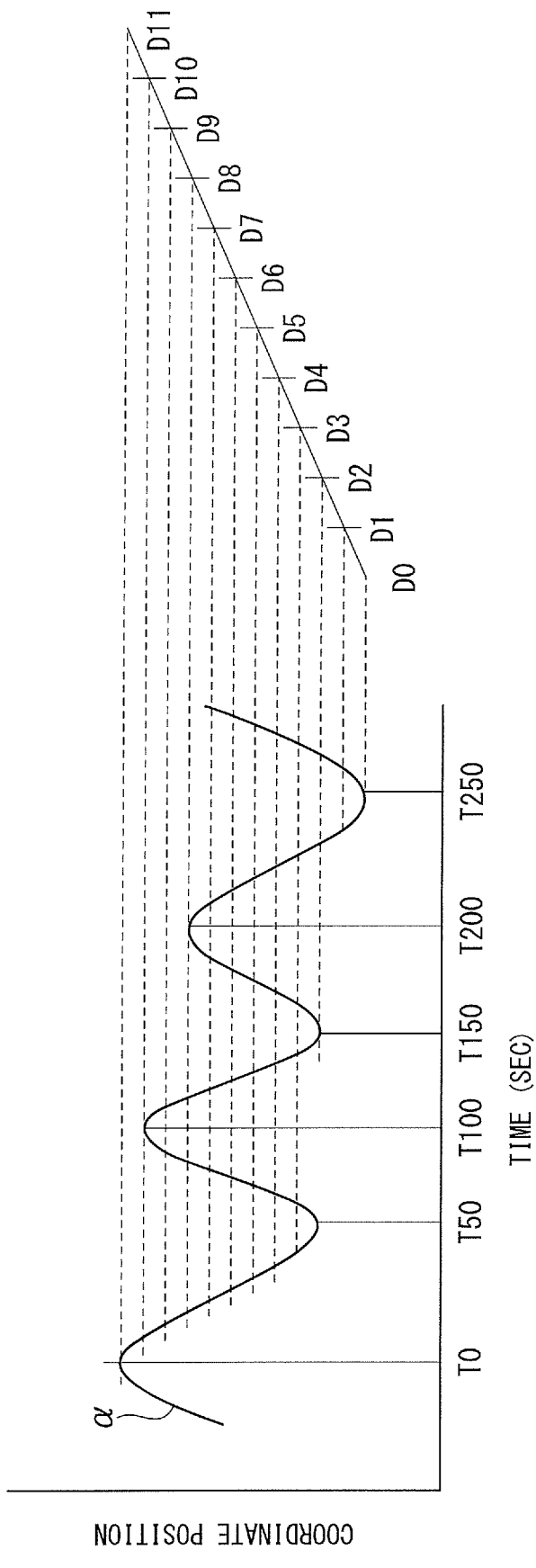
FIG. 10 is a view illustrating another modification example of a waveform of the coordinate position for selecting a reference image.

Here, as illustrated in FIG. 10, it is assumed that approximately three maximum exhalation positions and three maximum inhalation positions have appeared during three respirations. In this case, the fluoroscopic image TI in the range which includes the maximum inhalation position and the maximum exhalation position and in which the difference between the coordinate positions is maximized, here, in the range between the time T0 and a time T250 is selected as a reference image.

In the range between the time T0 and the time T250, the fluoroscopic image TI for more than half a respiration is included to be able to selected as a reference image. When reference images are selected from these many fluoroscopic images TI, for example, the coordinate position of the maximum inhalation position and the coordinate position of the maximum exhalation position in which the difference between the coordinate positions is maximized may be equally divided into a predetermined number of positions, and fluoroscopic images at positions corresponding to matching coordinate positions D0 to D11 may be selected as reference images.

For example, the fluoroscopic images TI of the coordinate positions D0 and D11 become the fluoroscopic images TI at the time T250 and T0. However, for example, the fluoroscopic image TI at the coordinate position D4 may be suitably selected from five fluoroscopic images TI between the time T0 and the time T50, between the time T5 and the time T100, between the time T100 and the time T150, between the time T150 and the time T200, and between the time T200 and the time T250. The selection method is not particularly limited. For example, the fluoroscopic image TI at the largest time may be selected, or the fluoroscopic image TI at the smallest time may be selected. The fluoroscopic image TI closest to the time of the maximum exhalation position or the maximum inhalation position may be selected, or a plurality of fluoroscopic images TI, here, the fluoroscopic images TI in one respiration, of three respirations, including the maximum number of fluoroscopic images TI may be selected. Alternatively, the fluoroscopic images TI may be selected as reference images equally from three respirations.

(Fourth Selection Form of Reference Image)

When a reference image is selected, while the fluoroscopic image TI is being captured, respirations of the object P may be in disorder due to coughing or sneezing, or respirations may become shallow sometimes. When a target position is identified, it is efficient that the fluoroscopic image TI of this case is not used as a reference image. Therefore, in a fourth selection form, the fluoroscopic image TI captured in the first selection form to the third selection form of a reference image while respirations are in disorder or are shallow before a reference image is selected from the fluoroscopic images TI is automatically or manually selected and is deleted from the selection target of a reference image.

When the fluoroscopic image TI captured while there is a disorder or the like of respirations of the object P is automatically selected, for example, the external respiratory waveform or the waveform of the target position is observed, and a disorder or the like of respirations of the object P may be detected, when the disorder of these waveforms is significant or when the fluctuation amount per unit time of these waveforms is significant and exceeds a predetermined threshold value. When the fluoroscopic image TI captured while there is a disorder or the like of respirations of the object P is manually selected, for example, a physician or the like may monitor these waveforms and the fluoroscopic images TI to determine and manually delete the fluoroscopic image TI captured while a disorder or the like of respirations of the object P.

According to the embodiment described above, the medical apparatus 100 includes the associator 131 that associates the tracking value obtained based on the respiratory phase of an object with the time-series fluoroscopic image, and the selector 132 that selects a reference image from the time-series fluoroscopic images based on the associated tracking value. Thus, it is possible to improve convenience at the time of selecting a reference image from a plurality of fluoroscopic images.

According to the embodiment, the medical apparatus 100 includes the input/display 120 that is capable of inputting one (one point) of the tracking values. The selector 132 selects the fluoroscopic images TI, as reference images, for one respiration of the object P including the respiratory phase corresponding to one of the tracking values input to the input/display 120. Accordingly, a reference image is selected by only inputting one point of the tracking values. Thus, it is possible to improve convenience at the time of selecting a reference image from a plurality of fluoroscopic images.

According to the medical apparatus 100 of the embodiment, the selector 132 selects a fluoroscopic image, as the reference image, in a range around the maximum exhalation position of the object P immediately before the respiratory phase corresponding to one point of the tracking values. Thus, it is possible to select a reference image in a favorable range having the fluoroscopic image at the maximum exhalation position included in the reference image. The maximum exhalation position may be substituted with the maximum inhalation position.

According to the embodiment, the medical apparatus 100 includes the input/display 120 that is capable of inputting one (one point) of the tracking values. The selector 132 selects a fluoroscopic image, as a reference image, in a range around the input maximum exhalation position when the tracking value corresponding to the maximum exhalation position of the object P is input to the input/display 120. Thus, it is possible to select a reference image in a favorable range having the fluoroscopic image at the maximum exhalation position included in the reference image. The maximum exhalation position may be substituted with the maximum inhalation position or an irradiation position.

According to the medical apparatus 100 of the embodiment, the selector 132 selects the equal number of fluoroscopic images, as the reference images, in the front and the rear of the maximum exhalation position. Thus, it is possible to select a reference image in a favorable range and the quantity having the fluoroscopic image at the maximum exhalation position included in the reference image. The maximum exhalation position may be replaced with the maximum inhalation position.

According to the medical apparatus 100 of the embodiment, the selector 132 selects the reference images including the fluoroscopic images of the maximum exhalation position and the maximum inhalation position, of a plurality of maximum exhalation positions and maximum inhalation positions, at which the difference between the maximum exhalation position and the maximum inhalation position is maximized when the maximum exhalation position and the maximum inhalation position are different from each other during several respirations of the object P. Thus, it is possible to prevent a reference image from being biased, and it is possible to contribute to accurate tracking of a lesion.

According to the medical apparatus 100 of the embodiment, the selector 132 rearranges the plurality of fluoroscopic images TI based on the tracking value and selects the fluoroscopic image TI, as a reference image, which is associated with the tracking value and is equally distant from the maximum value and the minimum value of the tracking value. Thus, it is possible to efficiently select reference images having different tracking values.

According to the medical apparatus 100 of the embodiment, the display controller 124 causes the gating window to be displayed in a manner of being superimposed on the fluoroscopic image and changes the color of the gating window when a gate-on signal is output. Thus, it is possible to plainly inform a physician or the like of an output of a gate-on signal.

According to the medical apparatus 100 of the embodiment, the display controller 124 causes the gating window to be displayed in a manner of being superimposed on the fluoroscopic image and changes the hue or the brightness of any of the inner region and the outer region of the gating window when a gate-on signal is output. Thus, it is possible to plainly inform a physician or the like of an output of a gate-on signal.

The medical apparatus 100 according to the embodiment further includes a notifier that issues notification by a sound or a vibration when a gate-on signal is output. Thus, it is possible to plainly inform a physician or the like of an output of a gate-on signal.

(Modification Example)

In each of the steps in the flowchart described in the foregoing embodiment as an example, unless it is against its nature, the execution order may be changed, a plurality of steps may be performed at the same time, or the steps may be performed in a different order every time the steps are performed.

In the foregoing embodiment, the therapeutic device 10 and the medical apparatus 100 are described as separate devices. However, the therapeutic device 10 and the medical apparatus 100 may be an integrated device. When the therapeutic device 10 and the medical apparatus 100 are separate devices, the output controller 150 may be a function built inside the medical apparatus 100.

One point may be input to a waveform associated with the fluoroscopic image TI. In ranges more than one respiration or in regions less than one respiration about this one point, the equal number of fluoroscopic images TI may be adopted in the front and the rear as reference images including the maximum exhalation position and the maximum inhalation position. In the fluoroscopic images TI, reference images may be selected for each group by grouping images of which the pixel values are close to each other. For example, as the position of a lesion in grouped reference images, the average position of the lesion in the reference images may be adopted.

When a target significantly moves and the target positions between the fluoroscopic images TI are significantly different from each other, an interpolation image may be inserted between the time-series fluoroscopic images TI. When an interpolation image is inserted between the time-series fluoroscopic images TI, information can be interpolated, so that a reference image can be efficiently selected. A smoothing button for executing smoothing to insert an interpolation image may be provided, and smoothing may be performed based on an operation of a physician or the like.

In the foregoing embodiment, a template is made by selecting a reference image from the waveform α of the coordinate position for one respiration. However, a template may be made by selecting a reference image from the waveform α of the coordinate position for less than one respiration, for example, the waveform α of the coordinate position for half a respiration. In this case, there is almost no change in the coordinate position in the vicinity of the maximum exhalation position and in the vicinity of the maximum inhalation position, but a relatively large change in the coordinate position is observed at positions away from the maximum exhalation position and the maximum inhalation. Therefore, less reference images may be selected in the vicinity of the maximum exhalation position and in the vicinity of the maximum inhalation position, and more reference images may be selected at positions away from the maximum exhalation position and the maximum inhalation position. Specifically, with reference to FIG. 10, less reference images may be selected in areas near D0 to D2 and D9 to D11 in the vicinity of the maximum exhalation position and in the vicinity of the maximum inhalation position, and more reference images may be selected in areas near D3 to D8. In this manner, even in a case of a selection image for half a respiration, a reference image can be efficiently selected and a template can be made by sorting the images to be selected. Even when a reference image is selected from the waveform of the coordinate position for one respiration or more, less reference images may be selected in the vicinity of the maximum exhalation position and in the vicinity of the maximum inhalation position, and more reference images may be selected at positions away from the maximum exhalation position and the maximum inhalation position.

When a reference image selected in the foregoing embodiment is used, for example, when a template is made from the reference image, a target position can be identified through the template matching method of comparing the fluoroscopic image TI acquired at the time of therapeutic irradiation and a template. Alternatively, a target position on the fluoroscopic image TI can be identified through machine learning of a reference image.

The control method for a medical apparatus described in the foregoing embodiment is a control method for a medical apparatus acquiring fluoroscopic images of an object captured in time series, and selecting reference images which include fluoroscopic images corresponding to a maximum exhalation position and a maximum inhalation position of the object from the plurality of acquired fluoroscopic images.

The program described in the foregoing embodiment is a program for causing a computer to acquire fluoroscopic images of an object captured in time series, and to select reference images which include fluoroscopic images corresponding to a maximum exhalation position and a maximum inhalation position of the object from the plurality of acquired fluoroscopic images.

According to the embodiment described above, it is possible to improve convenience at the time of selecting a reference image from a plurality of fluoroscopic images by having an acquirer (130) that acquires fluoroscopic images (TI) of an object (P) captured in time series, and a selector (132) that selects reference images which include fluoroscopic images corresponding to a maximum exhalation position and a maximum inhalation position of the object from the plurality of fluoroscopic images acquired by the acquirer.

The foregoing embodiment can be expressed as follows.

A medical apparatus is configured to include a hardware processor, and a storage device that stores a program.

The hardware processor executes the program to acquire fluoroscopic images of an object captured in time series, and to select reference images which include fluoroscopic images corresponding to a maximum exhalation position and a maximum inhalation position of the object from the plurality of acquired fluoroscopic images.

The embodiment of the present invention has been described. However, the embodiment is presented merely as an example and is not intended to limit the scope of the invention. The embodiment can be performed in various other forms, and various omissions, replacements, and changes can be performed within a range not departing from the gist of the invention. The embodiment and modifications thereof are included in the invention disclosed in Claims and a range equivalent thereto in a manner similar to being included in the scope and the gist of the invention.

EXPLANATION OF REFERENCES

1 Therapy system
10 Therapeutic device
11 Bed
12-1, 12-2 Radiation source
13-1, 13-2 Detector
14 Irradiation gate
15 Sensor
20 Therapeutic device-side controller
100 Medical apparatus
110 General controller
120 Input/display
122 Input operation acquirer
124 Display controller
130 Acquirer
131 Associator
132 Selector
136 Image processor
140 Target position identifier
150 Output controller
160 Storage

What is claimed is:

1. A medical apparatus comprising:
an acquirer configured to acquire fluoroscopic images of an object captured in time series;
a selector configured to select reference images which include fluoroscopic images corresponding to a maximum exhalation position and a maximum inhalation position of the object from the plurality of fluoroscopic images acquired by the acquirer; and
an associator configured to associate a tracking value obtained based on a respiratory phase of the object with the fluoroscopic images acquired by the acquirer.

2. The medical apparatus according to claim 1, further comprising:
a notifier configured to issue a notification by a sound or a vibration when an irradiation permission signal is output.

3. The medical apparatus according to claim 1, further comprising:
an inputter configured to receive one of the tracking values,
wherein the selector is configured to select fluoroscopic images, as the reference images, for a predetermined number of respirations of the object including the respiratory phases corresponding to the tracking values input to the inputter.

4. The medical apparatus according to claim 3,
wherein the selector is configured to select a fluoroscopic image, as the reference image, in a range around the maximum exhalation position or the maximum inhalation position of the object immediately before or immediately after the respiratory phase corresponding to the tracking value received by the inputter.

5. The medical apparatus according to claim 3,
wherein the selector is configured to select, as the reference image, a fluoroscopic image in a range around the received maximum exhalation position or the received maximum inhalation position when a tracking value received by the inputter is the tracking value corresponding to the maximum exhalation position or the maximum inhalation position of the object.

6. The medical apparatus according to claim 4,
wherein the selector is configured to select, as the reference image, a same number of fluoroscopic images before and after the maximum exhalation position or the maximum inhalation position.

7. The medical apparatus according to claim 1,
wherein the selector is configured to rearrange the plurality of fluoroscopic images acquired by the acquirer based on the tracking value and is configured to select, as the reference image, the fluoroscopic images which are associated with tracking values with an equal interval between a maximum value and a minimum value of the tracking values.

8. The medical apparatus according to claim 1,
wherein, when the maximum exhalation positions and the maximum inhalation positions are different over several respirations of the object, the selector is configured to select, from the plurality of maximum exhalation positions and the plurality of maximum inhalation positions in the several respirations, fluoroscopic images, as the reference images, at the maximum exhalation position and the maximum inhalation position at which a difference between the maximum exhalation position and the maximum inhalation position is the largest.

9. The medical apparatus according to claim 1, further comprising:
an excluder configured to exclude a fluoroscopic image corresponding to a position of respiratory disorder of the object from the fluoroscopic images to be selected by the selector.

10. The medical apparatus according to claim 1, further comprising:
a template maker configured to make a template based on the reference image selected by the selector.

11. The medical apparatus according to claim 1, further comprising:
a display controller configured to cause a display to display an image,
wherein the display controller causes an irradiation permission range to be displayed in a manner of being superimposed on the fluoroscopic image and changes a color of the irradiation permission range when a position of a tracking target spot is settled within the irradiation permission range and an irradiation permission signal is output.

12. The medical apparatus according to claim 1, further comprising:
a display controller configured to cause a display to display an image,
wherein the display controller causes an irradiation permission range to be displayed in a manner of being superimposed on the fluoroscopic image and changes a hue or brightness of any of an inner region or an outer region of the irradiation permission range when an irradiation permission signal is output.

13. A method executed by a medical apparatus, comprising:
acquiring fluoroscopic images of an object captured in time series;
selecting reference images which include fluoroscopic images corresponding to a maximum exhalation position and a maximum inhalation position of the object from the plurality of acquired fluoroscopic images; and
associating a tracking value obtained based on a respiratory phase of the object with the acquired fluoroscopic images.

14. The method according to claim 13, further comprising:
making a template based on the selected reference image.

* * * * *